(12) United States Patent
Benz et al.

(10) Patent No.: US 12,131,145 B2
(45) Date of Patent: Oct. 29, 2024

(54) SYSTEMS AND METHODS FOR PEER-TO-PEER AUTOMATIC SOFTWARE UPDATES

(71) Applicant: Hill-Rom Services, Inc., Batesville, IN (US)

(72) Inventors: Eric Benz, Sunman, IN (US); Archana Vaidyanathan, Batesville, IN (US); Rakesh Karunakaran, Batesville, IN (US); Unnati Ojha, Apex, NC (US); Bryan Weidman, Columbus, IN (US); Nicholas Comparone, Batesville, IN (US)

(73) Assignee: HILL-ROM SERVICES, INC., Batesville, IN (US)

( * ) Notice: Subject to any disclaimer, the term of this patent is extended or adjusted under 35 U.S.C. 154(b) by 64 days.

(21) Appl. No.: 17/936,139

(22) Filed: Sep. 28, 2022

(65) Prior Publication Data
US 2023/0100133 A1    Mar. 30, 2023

Related U.S. Application Data

(60) Provisional application No. 63/249,136, filed on Sep. 28, 2021.

(51) Int. Cl.
| | |
|---|---|
| *G06F 8/65* | (2018.01) |
| *G06F 8/61* | (2018.01) |
| *G16H 40/40* | (2018.01) |

(52) U.S. Cl.
CPC ............ *G06F 8/65* (2013.01); *G06F 8/61* (2013.01); *G16H 40/40* (2018.01)

(58) Field of Classification Search
CPC .......... G06F 8/60; G16H 40/40; G16H 40/67
(Continued)

(56) References Cited

U.S. PATENT DOCUMENTS

| | | | |
|---|---|---|---|
| 6,151,708 A * | 11/2000 | Pedrizetti | G06F 8/65 |
| | | | 717/173 |
| 7,734,717 B2 | 6/2010 | Saarimaki et al. | |

(Continued)

FOREIGN PATENT DOCUMENTS

| | | | |
|---|---|---|---|
| CN | 103517448 B | 12/2016 | |
| WO | 2012061406 A2 | 5/2012 | |
| WO | WO-2015018302 A1 * | 2/2015 | .......... G06F 11/1489 |

OTHER PUBLICATIONS

Zimmermann, Thomas, et al. "Mining version histories to guide software changes." IEEE Transactions on software engineering 31.6 (2005): pp. 429-445. (Year: 2005).*

(Continued)

*Primary Examiner* — Satish Rampuria
(74) *Attorney, Agent, or Firm* — DINSMORE & SHOHL LLP (57) ABSTRACT

A method to be performed by a processor of a first computing device includes detecting one or more computing devices remote from the first computing device, establishing a peer-to-peer connection with a second computing device from among the one or more computing devices, comparing a first version of a software program installed on the first computing device to a second version of the software program installed on the second computing device, and upon determination that the second version of the software program is more recent than the first version of the software program, receiving second installation software associated with the second version of the software program and executing the second installation software to install the second version of the software program onto the first computing device.

18 Claims, 4 Drawing Sheets

(58) Field of Classification Search
USPC .................................................. 717/120–178
See application file for complete search history.

(56) References Cited

U.S. PATENT DOCUMENTS

| | | | |
|---|---|---|---|
| 8,024,723 B2 | 9/2011 | Nahm et al. | |
| 9,575,741 B2 | 2/2017 | Chinnappan et al. | |
| 9,737,155 B2 | 8/2017 | Rawls-Meehan | |
| 9,940,436 B2* | 4/2018 | Nekoomaram | G16H 40/40 |
| 2012/0017206 A1* | 1/2012 | Ferguson | H04L 67/52 |
| | | | 714/1 |
| 2013/0036412 A1* | 2/2013 | Birtwhistle | G06F 8/65 |
| | | | 717/171 |
| 2014/0207844 A1 | 7/2014 | Mayo et al. | |
| 2015/0082295 A1* | 3/2015 | Collins, Jr. | G07C 3/00 |
| | | | 717/170 |
| 2017/0308568 A1* | 10/2017 | Laethem | G06F 8/65 |
| 2020/0082937 A1 | 3/2020 | Bodurka et al. | |
| 2021/0125713 A1 | 4/2021 | Audrain et al. | |

OTHER PUBLICATIONS

Kim, Sunghun, et al. "Predicting faults from cached history." 29th International Conference on Software Engineering (ICSE'07). IEEE, 2007.pp. 489-498 (Year: 2007).*

Huang, Guoyan, et al. "Automatic classification method for software vulnerability based on deep neural network." IEEE Access 7 (2019): pp. 28291-28298. (Year: 2019).*

Hicks, Michael, and Scott Nettles. "Dynamic software updating." ACM Transactions on Programming Languages and Systems (TOPLAS) 27.6 (2005): pp. 1049-1096. (Year: 2005).*

Hosek, Petr, and Cristian Cadar. "Safe software updates via multi-version execution." 2013 35th International Conference on Software Engineering (ICSE). IEEE, 2013.pp. 612-621 (Year: 2013).*

Aulbach, Stefan, et al. "Multi-tenant databases for software as a service: schema-mapping techniques." Proceedings of the 2008 ACM SIGMOD international conference on Management of data. 2008.pp. 1195-1206 (Year: 2008).*

International Search Report and Written Opinion with notification transmittal dated Jan. 27, 2023 in related International Application No. EP 22198109.5 (10 pages total).

* cited by examiner

SYSTEMS AND METHODS FOR PEER-TO-PEER AUTOMATIC SOFTWARE UPDATES

CROSS-REFERENCE TO RELATED APPLICATION

This application claims priority to U.S. Provisional Application No. 63/429,136 filed on Sep. 28, 2021, the entire contents of which is hereby incorporated by reference herein.

FIELD

The present disclosure generally relates to updating software and more particularly to systems and methods for peer-to-peer automatic software updates.

BACKGROUND

Medical facility equipment is often controlled by embedded software, which may need to be periodically updated with new software versions. However, some facilities such as hospitals may contain dozens or even hundreds of such equipment, which may all need to be updated when a new software version is available. Individually upgrading each piece of equipment in a facility with a new software version may be expensive and time-consuming, and as a result, may not be timely completed. This may lead to issues relating to malfunctioning equipment, improperly functioning equipment, deactivated features, vulnerabilities to malware, vulnerabilities to hacking, and/or the like.

BRIEF DESCRIPTION OF THE DRAWINGS

In one aspect, a method to be performed by a processor of a first computing device may include detecting one or more computing devices remote from the first computing device, establishing a peer-to-peer connection with a second computing device from among the one or more computing devices, and comparing a first version of a software program installed on the first computing device to a second version of the software program installed on the second computing device. Upon determination that the second version of the software program is more recent than the first version of the software program, the method may include receiving second installation software associated with the second version of the software program and executing the second installation software to install the second version of the software program onto the first computing device.

In another aspect, a method to be performed by a processor of a first computing device may include detecting a plurality of computing devices remote from the first computing device, establishing a peer-to-peer connection with each of the plurality of computing devices, comparing a version of a software program installed on the first computing device and versions of the software program installed on each of the plurality of computing devices, and determining which computing device of the first computing device and the plurality of computing devices has the most recent version of the software program. Upon determination that one of the plurality of computing devices has the most recent version of the software program, the method may include receiving installation software associated with the most recent version of the software program from the computing device determined to have the most recent version of the software program, and executing the installation software to install the most recent version of the software program onto the first computing device.

In another aspect, a device may include one or more processors and one or more non-transitory memory modules communicatively coupled to the one or more processors and storing machine-readable instructions. When executed, the machine-readable instructions may cause the one or more processors to at least detect one or more computing devices remote from the device, establish a peer-to-peer connection with a second computing device from among the one or more computing devices, and compare a first version of a software program installed on the device to a second version of the software program installed on the second computing device. Upon determination that the second version of the software program is more recent than the first version of the software program, the one or more processors may receive second installation software associated with the second version of the software program and execute the second installation software to install the second version of the software program onto the device.

In another aspect, a device may include one or more processors and one or more non-transitory memory modules communicatively coupled to the one or more processors and storing machine-readable instructions. When executed, the machine-readable instructions may cause the one or more processors to at least detect a plurality of computing devices remote from the device, establish a peer-to-peer connection with each of the plurality of computing devices, compare a version of a software program installed on the device and versions of the software program installed on each of the plurality of computing devices, and determine which of the device and the plurality of computing devices has the most recent version of the software program. Upon determination that one of the plurality of computing devices has the most recent version of the software program, the device may receive installation software associated with the most recent version of the software program from the one of the plurality of computing devices determined to have the most recent version of the software program, and execute the installation software to install the most recent version of the software program onto the device.

In another aspect, a system may include a first computing device and a second computing device remote from the first computing device. The first computing device may be configured to detect the second computing device, establish a peer-to-peer connection with the second computing device, and compare a first version of a software program installed on the first computing device to a second version of the software program installed on the second computing device. Upon determination that the second version of the software program is more recent than the first version of the software program, the first computing device may transmit a request to the second computing device for second installation software associated with the second version of the software program, receive the second installation software from the second computing device in response to the request, and execute the second installation software to install the second version of the software program onto the first computing device. The second computing device may be configured to establish the peer-to-peer connection with the first computing device, receive the request for the second installation software from the first computing device, and transmit the second installation software to the first computing device in response to the request.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, wherein like structure is indicated with like reference numerals and in which:

DETAILED DESCRIPTION

Medical facility equipment contains embedded software that controls their operation and functionality. This software is typically maintained by the manufacturer of the medical equipment, which may periodically produce new versions of the embedded software to improve the functionality of the medical equipment, to correct bugs, to activate features, to protect against malware, to protect against hacking, and/or the like. When a new software version is available, it must be installed onto medical equipment before the medical equipment can use the software.

One method of installing an updated software version onto medical equipment is to establish a hard-wired connection between the equipment and a device (e.g., a laptop computer) that can install the updated software onto the equipment. Once the updated software is installed to a first piece of equipment, the device can be disconnected from the first piece of equipment and connected to a second piece of equipment to install the updated software to the second piece of equipment. This procedure can be continued for every piece of equipment in the facility. However, if there is a large number of equipment in the facility, it can be very time-consuming to install the updated software on each piece of equipment in this manner.

Another option is to install updated software to a plurality of medical equipment remotely. However, many medical facilities do not have all of their equipment wirelessly connected to a single system from which updated software can be installed. Accordingly, installing software to a plurality of equipment remotely typically requires bringing a computer or other device to the facility and establishing a wireless server or hotspot with the device. Each piece of medical equipment in a vicinity of the wireless hotspot can connect to the device and the device can transmit the updated software to each connected piece of equipment. However, in a large facility, such a wireless hotspot will typically only be within range of a small number of the total number of pieces of medical equipment in the facility at any one time. As such, this procedure may need to be repeated many times at different locations within the facility in order to install the updated software to all of the medical equipment in the facility, which may also be time-consuming.

Accordingly, in embodiments disclosed herein, systems and method for peer-to-peer automatic software updates are provided. In embodiments, updated software may be installed on a single piece of equipment in a facility in a traditional manner, such as by one of the methods described above. Then, that single piece of equipment can connect to a second piece of equipment, in a peer-to-peer manner (e.g., utilizing Wi-Fi Direct), and can transfer the updated software to the second piece of equipment. The first piece of equipment may transfer the updated software to each piece of equipment within a range that can be communicated with using Wi-Fi Direct or any other peer-to-peer method. Then, each of those pieces of equipment may connect to other equipment that may not be within range of the first piece of equipment and provide the updated software. This process may be repeated to propagate the updated software to every piece of medical equipment throughout the entire facility. Thus, embodiments disclosed herein have a technical effect of propagating a software update to a plurality of pieces of medical equipment in a medical facility after the software update is installed on one piece of equipment in the facility.

While the present disclosure relates specifically to hospital beds, it should be understood that this is merely an example. That is, the systems and methods described herein may be used to deliver software updates to any types of equipment, including, but not limited to, overhead lifts, vital monitoring equipment, control devices, wall-mounted displays, nurses station equipment, surgical equipment, furniture, wheelchairs, and/or the like. Further, the systems and methods described herein may be used for updating other, non-medical equipment such as, for example, office equipment such as printers, fax machines, communications equipment, farm equipment, manufacturing equipment, and/or the like. In addition, while the present disclosure relates specifically to medical facilities such as hospitals, physician offices, urgent care centers, clinics, and the like, it should be understood that this is merely an example. That is, the systems and methods described herein may be located in other locations outside medical facilities, such as offices, factories, farms, and/or the like.

Figure 1:
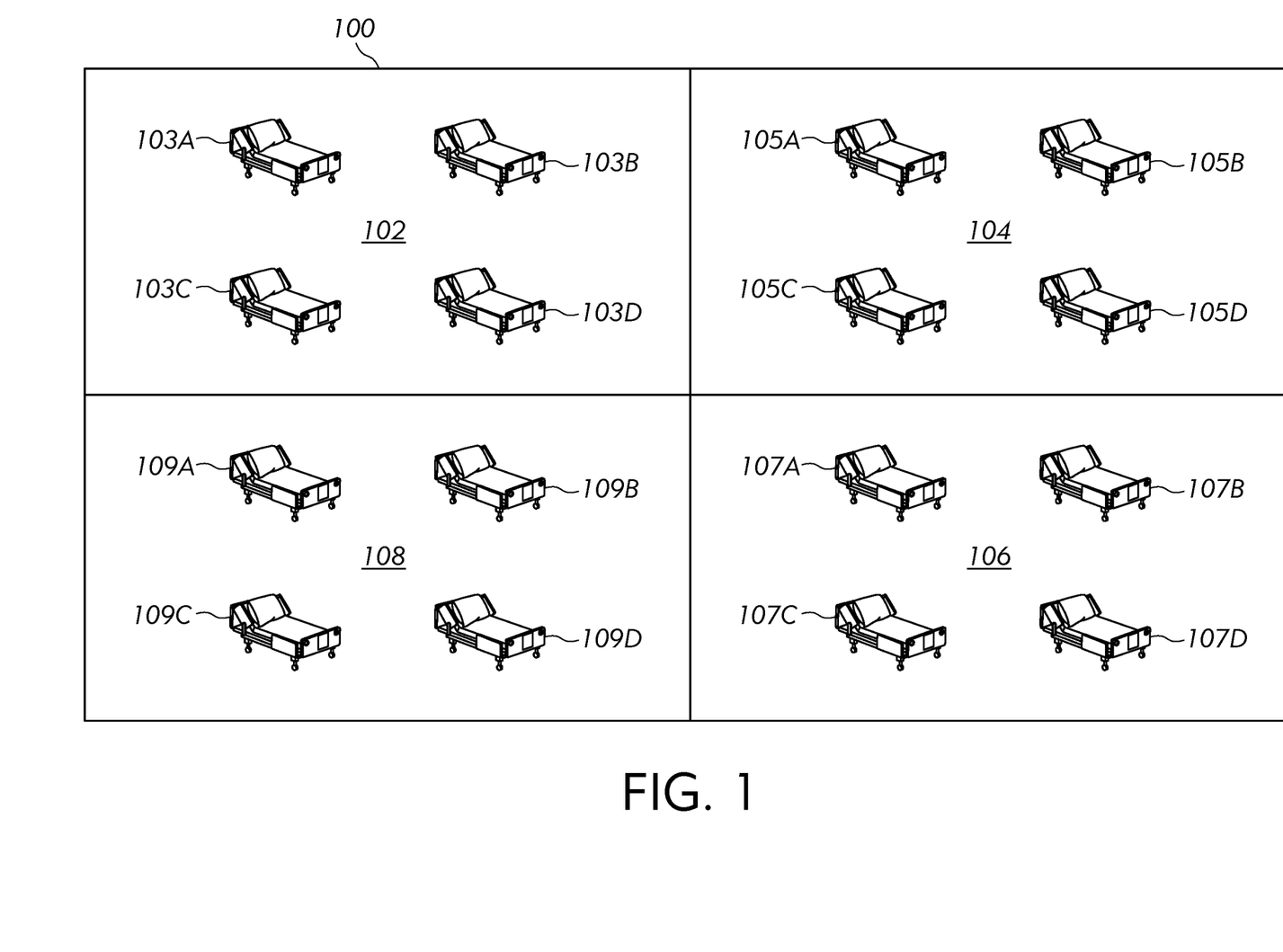
FIG. 1 schematically depicts an example hospital comprising a plurality of hospital beds, according to one or more embodiments shown and described herein.

FIG. 1 depicts an example of a hospital 100 containing a plurality of hospital beds 103 according to an embodiment. In the example of FIG. 1, the hospital 100 is divided into four sections, 102, 104, 106, 108, each section containing a plurality of hospital beds 103. In particular, section 102 contains beds 103A, 103B, 103C, 103D, section 104 contains beds 105A, 105B, 105C, 105D, section 106 contains beds 107A, 107B, 107C, 107D, and section 108 contains beds 109A, 109B, 109C, 109D. However, it should be understood that, in other examples, a hospital may contain any number of sections and/or any number of hospital beds.

In the example of FIG. 1, the sections may comprise different rooms, wings, floors, or other divisions of the hospital 100. In the example of FIG. 1, each bed within a particular section is within Wi-Fi Direct range of every other bed in that section. However, only certain beds in a particular section of the hospital 100 are in Wi-Fi Direct range of certain other beds in other sections, as explained in further detail below.

In the example of FIG. 1, each hospital bed in the hospital 100 contains embedded software that controls the operation of the hospital bed. When a new version of the embedded software becomes available, it is desirable to update the embedded software on each bed in the hospital 100. However, as explained above, it may not be desirable for service personnel to manually install the updated software on every bed in the hospital or even make a trip to the hospital to wirelessly push the software update to the beds. And hospital beds may not be Internet connected for security or other reasons. As such, as disclosed herein, systems and methods are provided for peer-to-peer automatic software updates whereby one bed that includes the updated software, when brought into the vicinity of the other beds not including the updated software automatically pushes the update to the other beds and the software is then propagated to all of the beds in the hospital 100 accordingly.

Figure 2:
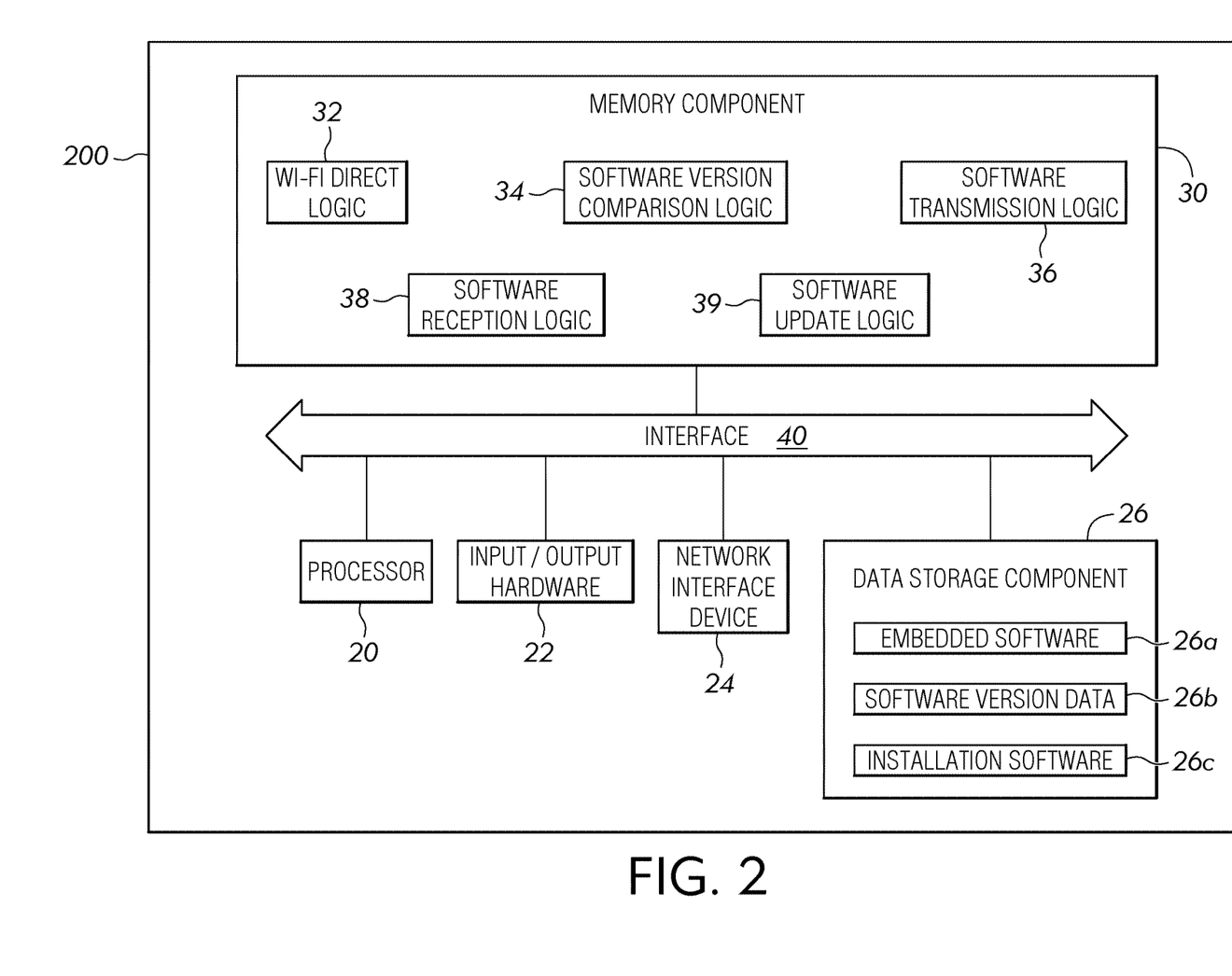
FIG. 2 schematically depicts an illustrative computing device integrated with a hospital bed according to one or more embodiments shown and described herein.

Turning now to FIG. 2, a schematic diagram of an example computing device 200 that may be integrated into or be a part of each of the hospital beds of FIG. 1. The computing device 200 described herein may be a computing system or a specialized device or system in various embodiments. Accordingly, while in some embodiments, the computing device 200 may be configured as a general purpose computer with the requisite hardware, software, and/or firmware, in some embodiments, the computing device 200 may be configured as a special purpose device or system designed specifically for performing particular tasks associated with operating a hospital bed, as well as the functionality described herein. While embodiments described herein are directed towards hospital beds, it should be understood that in other examples, the computing device 200 may be utilized with other devices or apparatuses that run embedded or other software. In these examples, the computing device 200 may be used to automatically upgrade software on such other devices or apparatuses in a peer-to-peer manner, using the techniques described herein.

As illustrated in FIG. 2, the computing device 200 includes a processor 20, input/output hardware 22, network interface hardware 24, a data storage component 26, and a non-transitory memory component 30. A local interface 40 is also included in FIG. 2 and may be implemented as a bus or other interface to facilitate communication among the components of the computing device 200. For example, the local interface 40 may communicatively couple the memory component 30 to the processor 20.

The processor 20, such as a central processing unit (CPU), may be the central processing unit of the computing device 200, performing calculations and logic operations to execute a program (e.g., embedded software). The processor 20, alone or in conjunction with the other components, may be an illustrative processing device, computing device, processor, or combinations thereof, including, for example, a multi-core processor, a microcontroller, a field-programmable gate array (FPGA), or an application-specific integrated circuit (ASIC). The processor 20 may include any processing component configured to receive and execute instructions (such as from the data storage component 26 and/or the memory component 30). In some embodiments, the processor 20 may comprise a plurality of processing devices.

The input/output hardware 22 may include a monitor, a keyboard, a mouse, a printer, a camera, a microphone, a speaker, a touch-screen, a motor controller, a solenoid and valve driver, an analog or a digital sensor (e.g., temperature, pressure, positional, etc.) and/or other device for receiving, sending, and/or presenting data, reading sensors or controlling motors, valves, solenoids and the like, particularly those used in medical devices, healthcare systems, and the like. For example, the input/output hardware 22 may include a serial bus, and/or another industry standard bus. In a particular embodiment, the input/output hardware 22 may be hardware that is certified as compliant with applicable industry standards.

The network interface hardware 24 may include any wired or wireless networking hardware, such as a modem, LAN port, wireless fidelity (Wi-Fi) card, WiMax card, mobile communications hardware, and/or other hardware for communicating with other networks and/or devices. For example, the network interface hardware 24 may be used to facilitate communication between external storage devices, user computing devices, server computing devices, external control devices, and/or the like via a network, such as, for example, a local network, the Internet, and/or the like. In particular, in the illustrated example, the network interface hardware 24 may be used to communicate with other beds in a peer-to-peer manner, for example, using a protocol such as Wi-Fi Direct. However, in other examples, the network interface hardware 24 may be used to communicate with other beds in a peer-to-peer manner using other communication protocols such as Bluetooth or near-field communication (NFC).

The data storage component 26 is generally a storage medium, and may contain one or more data repositories for storing data that is received and/or generated. The data storage component 26 may be any physical storage medium, including, but not limited to, a hard disk drive (HDD), memory (e.g., read-only memory (ROM), programmable read-only memory (PROM), random access memory (RAM), double data rate (DDR) RAM, flash memory, and/or the like), removable storage, a configuration file (e.g., text) and/or the like. While the data storage component 26 is depicted as a local device, it should be understood that the data storage component 26 may be a remote storage device, such as, for example, a server computing device, cloud-based storage device, or the like.

In the example of FIG. 2, the data storage component 26 includes embedded software 26a, software version data 26b, and installation software 26c. The embedded software 26a is software that controls the operation of the hospital bed associated with the computing device 200. In particular, the embedded software 26a may receive data from different sensors or components of the hospital bed related to patient activity or functionality of the hospital bed. The embedded software 26a may receive user input from patients, nurses, or others.

The embedded software 26a may analyze received data or user inputs and cause certain actions to occur based on the analysis. For example, the embedded software 26a may cause actuators to move certain components of the hospital in response to user input to change the position of the bed. In addition, the embedded software 26a may transmit a signal to a nurse indicating that patient attention is needed in response to certain patient activity. While in the illustrated example, the data storage component 26 stores embedded software 26a, it should be understood that in other examples, the data storage component 26 may store other types of software such as operating system software, application software, and the like, that may also be updated using the techniques described herein.

The software version data 26b is data indicating the version of the embedded software 26a that the computing device 200 is currently using. In some examples, the software version data 26b may include a version number. In other examples, the software version data 26b may include other types of data to indicate the version of the embedded software 26a being used by the computing device 200.

In embodiments, any time that the embedded software 26a is updated, the version of the updated embedded software being installed is stored as the software version data 26b. This may be compared to software version data on other hospital beds to determine whether other hospital beds have a more recent version of the embedded software 26a, as discussed in further detail below. As used herein, the terms "more recent" and "most recent" broadly connote a version of software that is more or most desired, which may be the version having the latest technical features, the correct version, or more generally, the version most appropriate and desired for use at a particular time with particular hardware.

The installation software 26c is software used to install the embedded software 26a. In some examples, the installation software 26c comprises an installation file (e.g., a binary file). In embodiments, whenever an updated version of the embedded software 26a is installed onto the computing device 200, the installation software used to install the embedded software 26a may also be stored in the data storage component 26 as the installation software 26c. As such, the installation software 26c can be transmitted to other hospital beds so that the latest version of the embedded software 26a can be installed on the other hospital beds, as discussed in further detail below.

The memory component 30 may be configured as a volatile and/or a nonvolatile computer readable medium and, as such, may include random access memory (including SRAM, DRAM, and/or other types of random access memory), flash memory, registers, compact discs (CD), digital versatile discs (DVD), and/or other types of storage components. Additionally, the memory component 30 may be configured to include various logic modules (each of which may be embodied as a computer program, firmware, or hardware, as an example).

The memory component 30 may include a plurality of logic modules or memory modules. Each of the logic modules may be embodied as a computer program, firmware, or hardware, as an example. In particular, included in the memory component is Wi-Fi Direct logic 32, software version comparison logic 34, software transmission logic 36, software reception logic 38, and software update logic 39.

The Wi-Fi Direct logic 32 may be used to establish a peer-to-peer connection between the computing device 200 and the computing device of one or more other hospital beds. In some examples, each bed in a hospital may comprise a computing device similar to the computing device 200 and the Wi-Fi Direct logic 32 may be used to establish a peer-to-peer connection between the computing device 200 of one hospital bed and a similar computing device of another hospital bed.

In the illustrated example, the Wi-Fi Direct logic 32 establishes a peer-to-peer connection using the Wi-Fi Direct standard. However, in other examples, the Wi-Fi Direct logic 32 may establish a peer-to-peer connection using other types of communication protocols (e.g., Bluetooth, near-field communication, and the like).

Wi-Fi Direct is a communication standard for peer-to-peer wireless connections that allows two devices to establish a direct Wi-Fi connection between them without an intermediary wireless access point. In another mode of operation, Wi-Fi Direct can be used to allow one device to act as a host and connect to a plurality of other devices simultaneously. In either mode of operation, devices can use Wi-Fi Direct to connect to one or more other devices in a peer-to-peer manner while still maintaining a standard Wi-Fi connection to a wireless network. As such, using Wi-Fi Direct allows hospital beds to connect to other hospital beds in a peer-to-peer manner for the purpose of updating embedded software while still maintaining a connection to a hospital Wi-Fi network, thereby not causing any disruption to the operation of the beds while the updated software installation occurs.

In some examples, the Wi-Fi Direct logic 32 may operate in a one-to-one mode of operation. In other examples, the Wi-Fi Direct logic 32 may operate in a one-to-many mode of operation. In the one-to-one mode of operation, the Wi-Fi Direct logic 32 may use the Wi-Fi Direct protocol to connect the computing device 200 to a single computing device of another hospital bed. Alternatively, in the one-to-many mode of operation, the Wi-Fi Direct logic 32 may use the Wi-Fi Direct protocol to simultaneously connect the computing device 200 to multiple computing device of other hospital beds.

In either mode of operation, the computing device 200 to a computing device of another hospital bed. In particular, the Wi-Fi Direct logic 32 may cause the network interface hardware 24 to detect other hospital beds within range of the computing device 200 (e.g., within the range for which Wi-Fi Direct connections are possible). That is, the computing device 200 may be able to detect other hospital beds within a certain range of the computing device 200.

After detecting one or more other hospital beds within range of the computing device 200, in the one-to-one mode of operation, the Wi-Fi Direct logic 32 may cause the network interface hardware 24 to establish a peer-to-peer connection with the computing device of one the detected hospital beds. After establishing a peer-to-peer connection with another hospital bed, the computing device 200 may determine whether the embedded software on the other hospital bed is a later version than the embedded software 26a on the computing device 200 and may update the software if appropriate, as explained in further detail below. The Wi-Fi Direct logic 32 may then close the connection and may establish a peer-to-peer connection with another hospital bed detected within range of the computing device 200. As such, the Wi-Fi Direct logic 32 may cause the computing device 200 to establish a peer-to-peer connection with each other hospital bed within range of the computing device 200 in turn.

In a large hospital, it is unlikely that any particular bed in a hospital will be in range of every other bed in the hospital. However, every bed in a hospital is likely to be in range of at least one other bed in the hospital. In particular, some beds in one section or one floor of a hospital may be within range of at least one hospital bed in another section or another floor of the hospital. For example, in FIG. 1, hospital bed 103D in section 102 of the hospital 100 may be within range of hospital bed 109B in section 108 and hospital bed 105C in section 104. As such, after updated software is installed on one hospital bed, that hospital may connect to other beds within its range and transfer the updated software to those beds. Each of those beds may then connect to other hospital beds and transfer the updated software to those beds. This process may be repeated until the updated software is propagated throughout the entire hospital.

In the one-to-many mode of operation, the Wi-Fi Direct logic 32 may use the Wi-Fi Direct protocol to cause the network interface hardware 24 to connect to another hospital bed acting as a host, or to cause the network interface hardware 24 to act as a host that multiple other hospital beds can connect to. In some examples, certain beds in a hospital may be designated as hosts for purposes of one-to-many operation of Wi-Fi Direct. Other beds within range of a designated host bed may then connect to the host bed using the Wi-Fi Direct protocol. In other examples, the Wi-Fi Direct logic 32 may determine a host for one-to-many operation of Wi-Fi Direct based on which beds are within range of the computing device 200. For example, different hospital beds may be assigned a priority and the hospital bed with the highest priority may be assigned as the host among a group of hospital beds. For example, hospital beds may be assigned a priority based on their location, their hardware, or other properties of the hospital beds. In other examples, a host may be determined by other methods (e.g., a host may be randomly assigned among a group of hospital beds within range of each other).

Referring still to FIG. 2, the software version comparison logic 34 may compare the version of the embedded software 26a installed on the computing device 200 to the version of the embedded software installed on another hospital bed after establishing a peer-to-peer connection to that hospital bed. As explained above, the software version data 26b includes the software version of embedded software 26a installed on the computing device 200. Thus, after establishing a peer-to-peer connection with another hospital bed, the software version comparison logic 34 may compare the version of embedded software installed on the two hospital beds. For example, the software version comparison logic 34 may cause the network interface hardware 24 to send a query to the other hospital bed requesting the version of the embedded software running on that hospital bed. The other hospital bed may transmit the version of the version of its embedded software back to the computing device 200. The software version comparison logic 34 may then compare the version of the embedded software running on the other hospital bed to the software version data 26b of the computing device 200.

In particular, in the one-to-one mode of operation in which two hospital beds are connected in a peer-to-peer manner, the software version comparison logic 34 may determine whether one of the hospital beds has a more recent version of the embedded software 26a than the other hospital bed. In the one-to-many mode of operation, in which a plurality of hospital beds are simultaneously connected to a host, the software version comparison logic 34 may determine which hospital bed among the host hospital bed and the plurality of hospital beds connected to the host has the most recent version of the embedded software 26a.

Referring still to FIG. 2, the software transmission logic 36 may cause the network interface hardware 24 to transfer the installation software 26c to another hospital bed that the computing device 200 is connected to (referred to herein as a connected hospital bed). In particular, the software transmission logic 36 may cause the network interface hardware 24 to transfer the installation software 26c to a connected hospital bed upon determination that the version of the embedded software 26a installed on the computing device 200 is more recent than the version of the embedded software installed on the connected hospital bed. In particular, the software transmission logic 36 may cause the network interface hardware 24 to transfer the installation software 26c using the Wi-Fi Direct protocol. As such, the connected hospital bed may receive the installation software, which it may execute in order to install the newer version of the embedded software. By different hospital beds connecting to other hospital beds in series, as explained above, the software transmission logic 36 of each bed in a hospital may be used to propagate a software update throughout all beds of a hospital.

Referring still to FIG. 2, the software reception logic 38 may cause the network interface hardware 24 to receive installation software for the embedded software installed on the connected hospital bed upon determination that the version of the embedded software installed on the connected hospital bed is more recent than the version of the embedded software 26a installed on the computing device 200. In particular, the software reception logic 38 may cause the network interface hardware 24 to receive the installation software using the Wi-Fi Direct protocol. The software reception logic 38 may then store the received installation software in the data storage component 26. In some examples, the software reception logic 38 may cause the network interface hardware 24 to transmit a request to the connected hospital bed for the installation software for the embedded software installed on the connected hospital bed and may receive the installation software transmitted by the connected hospital bed in response to the request.

In some examples, the software reception logic 38 may also receive installation software for a new version of the embedded software 26a provided by a service technician or other individual via a hardwired connection or wireless signal. That is, the first hospital bed in a hospital to receive a particular software upgrade may receive the software upgrade from a service technician via the software reception logic 38. The first hospital bed may then propagate the new version of the software to other beds in the hospital according to the techniques described herein.

In some examples, a service technician may transfer updated software to the computing device 200 using a mobile computing device (e.g., a smartphone). The updated software transferred from the mobile computing device to the computing device 200 may be received by the software reception logic 38. In some examples, a mobile computing device may be directly connected to the computing device 200 (e.g., by establishing a wired connection between the smartphone and a USB or other port of the computing device 200). In other examples, a mobile computing device may establish a wireless connection to the computing device 200 and updated software may be transferred via the wireless connection.

In some examples, a mobile computing device may establish a wireless hotspot and the computing device 200 may connect to the wireless hotspot. The mobile computing device may then authenticate the computing device 200 (e.g., with a username and password) and may establish an SSH, SFTP, or other connection with the computing device 200. The smartphone may then transfer the updated software to the computing device 200 over the wireless connection. In some examples, the smartphone may run an application that allows a user to monitor and/or control the file transfer via a software interface. Accordingly, updated software may be transferred from a smartphone to the computing device 200 without the need to establish a hardwired connection. Once the updated software is transferred to the computing device 200, the software may be received by the software reception logic 38. The updated software may then be transferred to other hospital beds in a peer-to-peer manner, as disclosed herein.

Referring still to FIG. 2, the software update logic 39 may execute the installation software received by the software reception logic 38 in order to update the embedded software 26a on the computing device 200. This may allow the computing device 200 to upgrade to the most recent version of the embedded software received from another hospital bed in a peer-to-peer manner. As such, the embedded software 26*a* on the computing device 200 can be automatically upgraded to the latest version without the need for a service technician to manually upgrade the embedded software 26*a* on the computing device 200.

Figure 3:
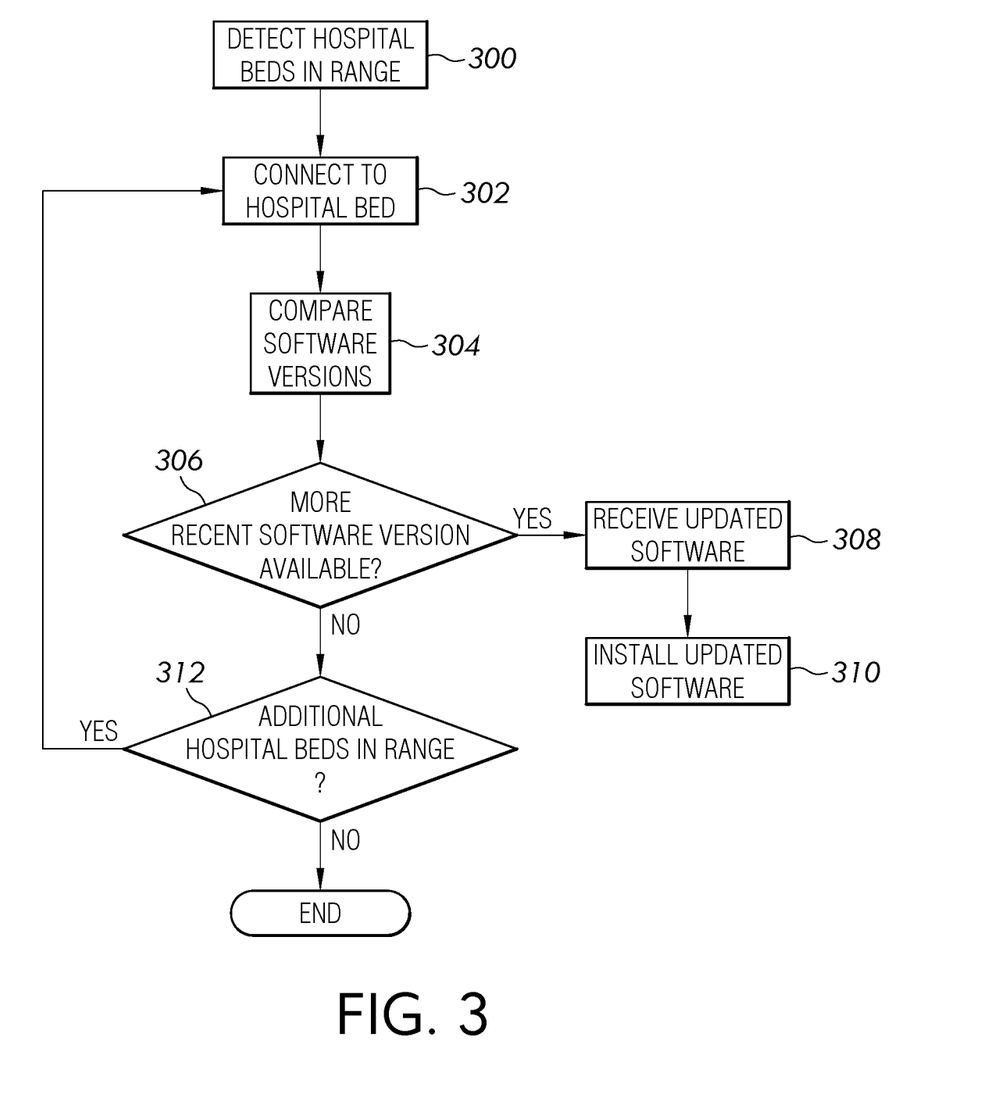
FIG. 3 depicts a flow diagram of an illustrative method to be performed by the computing device of FIG. 2 to automatically update software.

FIG. 3 depicts a flow diagram of an illustrative method of automatically updating software in a peer-to-peer manner that may be performed by the computing device 200 of FIG. 2. In particular, the example of FIG. 3 illustrates a method that may be performed by the computing device 200 in a one-to-one mode of operation.

At block 300, the Wi-Fi Direct logic 32 of FIG. 3 detects other hospital beds that are within Wi-Fi Direct connection range of the computing device 200. For example, the Wi-Fi Direct logic 32 may cause the network interface hardware 24 of FIG. 2 to send out a query to computing devices of other hospital beds. The computing device of any hospital bed within Wi-Fi Direct range may receive the query and may transmit a response to the query back to the computing device 200. Every response to such a query received by the computing device 200 may indicate a hospital bed within range of the computing device 200.

At block 302, the Wi-Fi Direct logic 32 causes the network interface hardware 24 to connect to the computing device of one of the detected hospital beds within range of the computing device 200. In particular, the Wi-Fi Direct logic may cause the network interface hardware 24 to establish a peer-to-peer connection between the computing device 200 and the computing device of one of the detected hospital beds using the Wi-Fi Direct protocol.

At block 304, the software version comparison logic 34 of FIG. 2 compares the version of the embedded software 26*a* installed on the computing device 200 to the version of the embedded software installed on the hospital bed that the computing device 200 is connected to (the connected hospital bed). For example, the software version comparison logic 34 may cause the network interface hardware 24 to query the connected hospital bed for the version of embedded software running on the connected hospital bed. The connected hospital bed may respond to the query with an indication of the software version running on the connected hospital bed and the software version comparison logic 34 of the computing device 200 may compare the version of embedded software indicated by the response received to such a query to the software version data 26*b*.

At block 306, the software version comparison logic 34 determines whether the connected hospital bed has a more recent version of the embedded software than the computing device 200. If the connected hospital bed has a more recent version of the embedded software than the computing device 200 ("YES" at block 306), then control passes to block 308. If the connected hospital bed does not have a more recent version of the embedded software than the computing device 200 ("NO" at block 306), then control passes to block 312.

At block 308, after the software version comparison logic 34 determines that the connected hospital bed has a more recent version of the embedded software than the computing device 200, the software reception logic 38 receives an installation file for the version of the embedded software installed on the connected hospital bed and stores the installation file in the data storage component 26. For example, the software reception logic 38 may cause the network interface hardware 24 to transmit a request to the connected hospital bed for the installation file associated with the embedded software installed on the connected hospital bed. The connected hospital bed may transmit the installation file in response to the request and the transmitted installation file may be received by the software reception logic 38.

Then, at block 310, the software update logic 39 of FIG. 2 executes the received installation file to upgrade the embedded software 26*a* to the version received from the connected hospital bed. The software upgrade logic 39 may also store the version of the embedded software 26*a* to which the computing device 200 was upgraded (e.g., a version number) in the data storage component 26 as the software version data 26*b*. In some examples, if the software version comparison logic 34 determines that the computing device 200 has a more recent version of the embedded software than the connected hospital bed, the software transmission logic 36 may transmit the installation software 26*c* to the connected hospital bed.

At block 312, after the software version comparison logic 34 determines that the connected hospital bed does not have a more recent version of the embedded software than the computing device 200, the Wi-Fi Direct logic 32 determines whether there are additional hospital beds within range of the computing device 200 that have not yet been connected to. If the Wi-Fi Direct logic 32 determines that there are additional hospital beds within range of the computing device 200 that have not yet been connected to ("YES" at block 312), then control returns to block 302 and the computing device 200 connects to a different hospital bed. As such, the computing device 200 may cycle through and connect to each hospital bed within range of the computing device 200 and determine whether any of the hospital beds have updated software. As such, if any hospital beds within range of the computing device 200 have received updated software, the computing device 200 will be able to receive the updated software.

If the Wi-Fi Direct logic 32 determines that there are no additional hospital beds within range of the computing device 200 that have not yet been connected to ("NO" at block 312), that is the computing device 200 has cycled through all of the hospital beds within range, then the method of FIG. 3 ends.

The method of FIG. 3 may be performed periodically by the computing device of each bed in a hospital. For example, the method of FIG. 3 may be performed once per hour, or once per day, or at any other interval. Accordingly, in order to upgrade the software of every bed in a hospital, a service technician may need only to upgrade the software of one bed in the hospital. The software of the other beds in the hospital will then be automatically upgraded by the method of FIG. 3. In some examples, the method of FIG. 3 may be performed by the computing device of a hospital bed upon some detected event, such as detection of a new hospital bed within range.

For example, in the hospital 100 of FIG. 1, a service technician may upgrade the software of hospital bed 103A. Hospital bed 103A may be within Wi-Fi Direct range of the other beds in section 102 of the hospital 100. As such, each of beds 103B, 103C, and 103D may connect to bed 103A and receive the updated software from bed 103A according to the method of FIG. 3.

Furthermore, in the example of FIG. 1, bed 103B may be in range of bed 105A and bed 103C may be in range of bed 109A. As such, bed 105A may connect to and receive the updated software from bed 103B and bed 109A may connect to and receive the updated software from bed 103C.

Bed 109A may then transmit the updated software to the other beds in section 108 of the hospital 100 and bed 105A may transmit the updated software to the other beds in section 104. Bed 105C may be in range of bed 107A and may subsequently transfer the updated software to bed 107A. Bed 107A may then transmit the updated software to the other beds of section 106. Accordingly, after installing updated software on a single bed in the hospital 100, the method of FIG. 3 may cause the updated software to be propagated to every other bed in the hospital 100.

Figure 4:
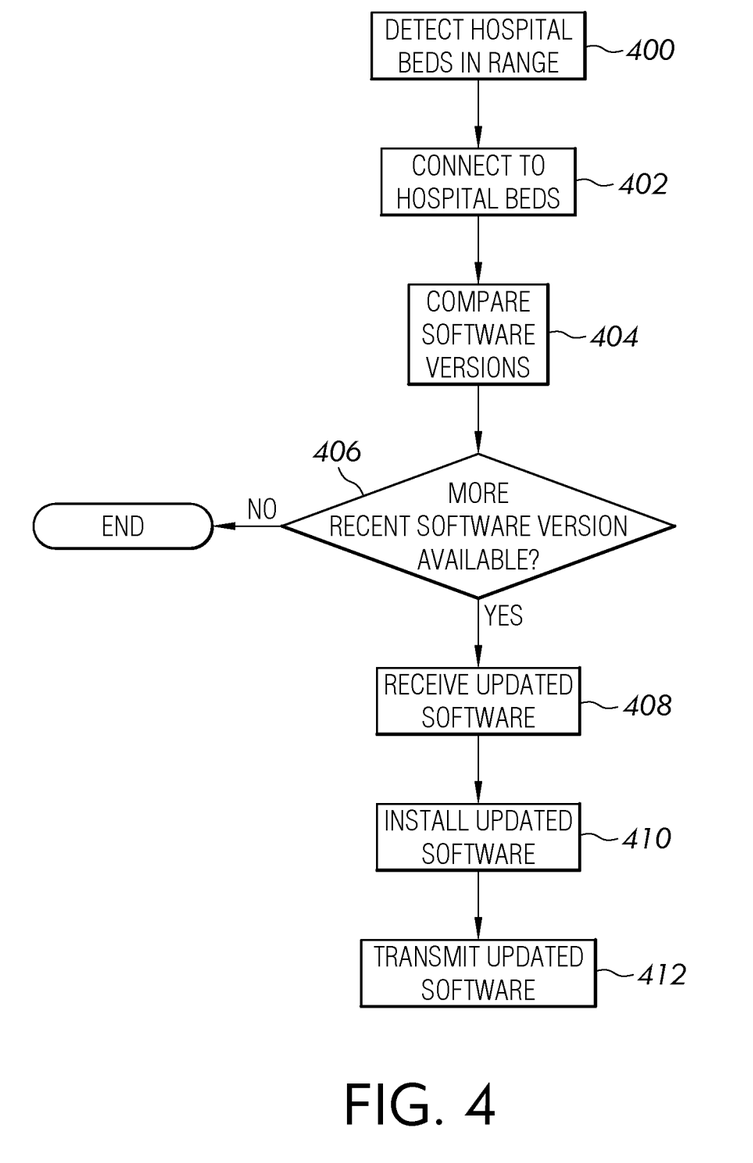
FIG. 4 depicts a flow diagram of another illustrative method to be performed by the computing device of FIG. 2 to automatically update software.

FIG. 4 depicts a flow diagram of another illustrative method of automatically updating software in a peer-to-peer manner that may be performed by the computing device 200 of FIG. 2. In particular, the example of FIG. 4 illustrates a method performed by the computing device 200 in a one-to-many mode of operation. In the example of FIG. 4, the computing device 200 acts as the host in the one-to-many mode of operation.

At block 400, the Wi-Fi Direct logic 32 of FIG. 2 detects other hospital beds within range of the computing device 200. Then, at block 402, the Wi-Fi Direct logic 32 causes the network interface hardware 24 of FIG. 2 to simultaneously connect to the computing device of each of the detected hospital beds within range of the computing device 200. In particular, the Wi-Fi Direct logic causes the network interface hardware 24 to connect to each of the detected hospital beds using the Wi-Fi Direct protocol.

At block 404, the software version comparison logic 34 of FIG. 2 compares the version of the embedded software installed on the computing device 200 and the version of the embedded software installed on each of connected hospital beds, for example, using the techniques described above. At block 406, the software version comparison logic 34 determines whether the computing device 200 or any of the connected hospital beds have a more recent version of the embedded software than any of the other hospital beds. That is, the software version comparison logic 34 identifies the connected hospital bed that has the most recent version of the embedded software.

If the software version comparison logic 34 determines that the computing device 200 and all of the connected hospital beds have the same version of the embedded software ("NO" at block 406), then the method of FIG. 4 ends. Alternatively, if the software version comparison logic 34 determines that the computing device 200 and all of the connected hospital beds do not have the same version of the embedded software, meaning that at least one of the hospital beds has a more recent version of the embedded software than at least one of the other hospital beds ("YES" at block 406), then control passes to block 408.

At block 408, the software reception logic 38 of FIG. 2 identifies which of the connected hospital beds has the most recent version of the embedded software. The software reception logic 38 then receives the installation file associated with the installed embedded software for the identified hospital bed and stores the received installation file on the data storage component 26. If multiple connected hospital beds have the most recent version of the embedded software, then the software reception logic 38 may receive the installation file from any one of the hospital beds that has the most recent version of the embedded software. Then, at block 410, the software update logic 39 of FIG. 2 executes the received installation file to install the most recent version of the embedded software onto the computing device 200.

The software upgrade logic 39 may also store the version of the embedded software 26a to which the computing device 200 was upgraded (e.g., a version number) in the data storage component 26 as the software version data 26b. If the computing device 200 already has the most recent version of the embedded software, then blocks 408 and 410 may be omitted.

At block 412, the software transmission logic 36 transmits the installation file 26c, which is now the installation file for the most recent version of the embedded software, to each of the connected hospital beds that do now already have the most recent version of the embedded software. After receiving the installation file 26c, each of those connected hospital beds may execute the installation file to upgrade their embedded software to the latest version.

The method of FIG. 4 may be executed periodically (e.g., once per hour, once per day). As such, when any bed in a hospital receives updated software, the method of FIG. 4 may cause the software to be propagated to every other bed in the hospital, in a similar manner as described above with respect to FIG. 3. In some examples, the method of FIG. 4 may begin when a hospital bed detects a new bed within range.

It should now be understood that embodiments described herein comprise systems and methods for peer-to-peer automatic software updates. In a one-to-one mode of operation, the computing device of a hospital bed may detect other hospital beds within Wi-Fi Direct connection range. The computing device may then connect to each of the detected hospital beds in sequence using the Wi-Fi Direct protocol. After connecting to a hospital bed, the computing device may determine whether one of the hospital beds has a more recent version of embedded software than the other hospital bed. If so, the hospital bed with the more recent version of the embedded software may transfer installation software associated with the embedded software to the other hospital bed, which may execute the installation software to upgrade the hospital bed to the more recent version of the embedded software.

In a one-to-many mode of operation, a computing device of one hospital bed may act as a host and may simultaneously connect to each other hospital bed within range of the host using the Wi-Fi Direct protocol. The host computing device may then identify the computing device of the hospital bed having the most recent version of the embedded software. The host may download installation software of the most recent version of the embedded software and execute the installation software to upgrade the embedded software version of the host hospital bed. The host computing device may then transfer the installation software to each connected hospital bed that does not already have the most recent version of the embedded software. Each of these hospital beds may then execute the installation software to upgrade the hospital bed to the most recent version of the embedded software.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

Further aspects of the invention are provided by the subject matter of the following clauses.

A method to be performed by a processor of a first computing device, comprising: detecting one or more computing devices remote from the first computing device; establishing a peer-to-peer connection with a second computing device from among the one or more computing devices; comparing a first version of a software program installed on the first computing device to a second version of the software program installed on the second computing device; and upon determination that the second version of the software program is more recent than the first version of the software program, receiving second installation software associated with the second version of the software program and executing the second installation software to install the second version of the software program onto the first computing device.

The method of any preceding clause, wherein the software program comprises embedded software.

The method of any preceding clause, wherein the first computing device is associated with a first hospital bed and the second computing device is associated with a second hospital bed.

The method of any preceding clause, further comprising: establishing the peer-to-peer connection with the second computing device using Wi-Fi Direct protocol.

The method of any preceding clause, further comprising: upon determination that the second version of the software program is more recent than the first version of the software program, storing a version number associated with the second version of the software program.

The method of any preceding clause, further comprising, upon determination that the first version of the software program is more recent than the second version of the software program, transmitting first installation software associated with the first version of the software program to the second computing device.

The method of any preceding clause, further comprising, upon determination that the first version of the software program is the same as the second version of the software program: terminating the peer-to-peer connection with the second computing device; establishing a second peer-to-peer connection with a third computing device from among the one or more computing devices; comparing the first version of the software program installed on the first computing device to a third version of the software program installed on the third computing device; and upon determination that the third version of the software program is more recent than the first version of the software program, receiving third installation software associated with the third version of the software program and executing the third installation software to install the third version of the software program onto the first computing device.

The method of any preceding clause, further comprising: periodically performing the steps of the method at a predetermined interval.

A method to be performed by a processor of a first computing device, comprising: detecting a plurality of computing devices remote from the first computing device; establishing a peer-to-peer connection with each of the plurality of computing devices; comparing a version of a software program installed on the first computing device and versions of the software program installed on each of the plurality of computing devices; determining which computing device of the first computing device and the plurality of computing devices has the most recent version of the software program; and upon determination that one of the plurality of computing devices has the most recent version of the software program, receiving installation software associated with the most recent version of the software program from the computing device determined to have the most recent version of the software program, and executing the installation software to install the most recent version of the software program onto the first computing device.

The method of any preceding clause, further comprising, after receiving the installation software: storing the installation software; and transmitting the installation software to each of the plurality of computing devices that does not have the most recent version of the software program.

The method of any preceding clause, further comprising: storing a version number associated with the most recent version of the software program.

The method of any preceding clause, further comprising: upon determination that the first computing device has the most recent version of the software program, transmitting the installation software associated with the most recent version of the software program to each of the plurality of computing devices that does not have the most recent version of the software program.

The method of any preceding clause, wherein the software program comprises embedded software.

The method of any preceding clause, wherein the first computing device is associated with a first hospital bed and each of the plurality of computing devices is associated with a different hospital bed.

The method of any preceding clause, further comprising: establishing the peer-to-peer connection with each of the plurality of computing devices using Wi-Fi Direct protocol.

The method of any preceding clause, further comprising: periodically performing the steps of the method at a predetermined interval.

A device comprising: one or more processors; and one or more non-transitory memory modules communicatively coupled to the one or more processors and storing machine-readable instructions that, when executed, cause the one or more processors to at least: detect one or more computing devices remote from the device; establish a peer-to-peer connection with a second computing device from among the one or more computing devices; compare a first version of a software program installed on the device to a second version of the software program installed on the second computing device; and upon determination that the second version of the software program is more recent than the first version of the software program, receive second installation software associated with the second version of the software program and execute the second installation software to install the second version of the software program onto the device.

The device of any preceding clause, wherein the software program comprises embedded software.

The device of any preceding clause, wherein the device is associated with a first hospital bed and the second computing device is associated with a second hospital bed.

The device of any preceding clause, wherein the instructions further cause the one or more processors to: establish the peer-to-peer connection with the second computing device using Wi-Fi Direct protocol.

The device of any preceding clause, wherein the instructions further cause the one or more processors to: upon determination that the second version of the software program is more recent than the first version of the software program, store a version number associated with the second version of the software program.

The device of any preceding clause, wherein the instructions further cause the one or more processors to: upon determination that the first version of the software program is more recent than the second version of the software program, transmit first installation software associated with the first version of the software program to the second computing device.

The device of any preceding clause, wherein the instructions further cause the one or more processors to: upon determination that the first version of the software program is the same as the second version of the software program: terminate the peer-to-peer connection with the second computing device; establish a second peer-to-peer connection with a third computing device from among the one or more remote computing devices; compare the first version of the software program installed on the device to a third version of the software program installed on the third computing device; and upon determination that the third version of the software program is more recent than the first version of the software program, receive third installation software associated with the third version of the software program and executing the third installation software to install the third version of the software program onto the device.

A device comprising: one or more processors; and one or more non-transitory memory modules communicatively coupled to the one or more processors and storing machine-readable instructions that, when executed, cause the one or more processors to at least: detect a plurality of computing devices remote from the device; establish a peer-to-peer connection with each of the plurality of computing devices; compare a version of a software program installed on the device and versions of the software program installed on each of the plurality of computing devices; determine which of the device and the plurality of computing devices has the most recent version of the software program; and upon determination that one of the plurality of computing devices has the most recent version of the software program, receive installation software associated with the most recent version of the software program from the one of the plurality of computing devices determined to have the most recent version of the software program, and execute the installation software to install the most recent version of the software program onto the device.

The device of any preceding clause, wherein the instructions further cause the one or more processors to: store the installation software; and transmit the installation software to each of the plurality of computing devices that does not have the most recent version of the software program.

The device of any preceding clause, wherein the instructions further cause the one or more processors to: store a version number associated with the most recent version of the software program.

The device of any preceding clause, wherein the instructions further cause the one or more processors to: upon determination that the device has the most recent version of the software program, transmit the installation software associated with the most recent version of the software program to each of the plurality of computing devices that does not have the most recent version of the software program.

The device of any preceding clause, wherein the software program comprises embedded software.

The device of any preceding clause, wherein the device is associated with a first hospital bed and each of the plurality of computing devices is associated with a different hospital bed.

The device of any preceding clause, wherein the instructions further cause the one or more processors to: establish the peer-to-peer connection with each of the plurality of computing devices using Wi-Fi Direct protocol.

A system comprising a first computing device and a second computing device remote from the first computing device, wherein: the first computing device is configured to: detect the second computing device; establish a peer-to-peer connection with the second computing device; compare a first version of a software program installed on the first computing device to a second version of the software program installed on the second computing device; and upon determination that the second version of the software program is more recent than the first version of the software program, transmit a request to the second computing device for second installation software associated with the second version of the software program, receive the second installation software from the second computing device in response to the request, and execute the second installation software to install the second version of the software program onto the first computing device; and wherein the second computing device is configured to: establish the peer-to-peer connection with the first computing device; receive the request for the second installation software from the first computing device; and transmit the second installation software to the first computing device in response to the request.

The system of any preceding clause, wherein the software program comprises embedded software.

The system of any preceding clause, wherein the first computing device is associated with a first hospital bed and the second computing device is associated with a second hospital bed.

The system of any preceding clause, wherein the first computing device is further configured to: establish the peer-to-peer connection with the second computing device using Wi-Fi Direct protocol.

The system of any preceding clause, wherein the first computing device is further configured to: upon determination that the second version of the software program is more recent than the first version of the software program, store a version number associated with the second version of the software program.

The system of any preceding clause, wherein the first computing device is further configured to: upon determination that the first version of the software program is more recent than the second version of the software program, transmit first installation software associated with the first version of the software program to the second computing device.

The system of any preceding clause, wherein the first computing device is further configured to, upon determination that the first version of the software program is the same as the second version of the software program: terminate the peer-to-peer connection with the second computing device; establish a second peer-to-peer connection with a third computing device; compare the first version of the software program installed on the first computing device to a third version of the software program installed on the third computing device; and upon determination that the third version of the software program is more recent than the first version of the software program, receive third installation software associated with the third version of the software program and execute the third installation software to install the third version of the software program onto the first computing device.

What is claimed is:

1. A method to be performed by a processor of a first computing device, comprising:
   detecting one or more computing devices remote from the first computing device associated with a first hospital bed;

automatically establishing a peer-to-peer connection with a second computing device associated with a second hospital bed from among the one or more computing devices;

comparing a first version of a software program installed on the first computing device to a second version of the software program installed on the second computing device; and upon determination that the second version of the software program is more recent than the first version of the software program, receiving second installation software associated with the second version of the software program from the second computing device, and executing the second installation software to install the second version of the software program onto the first computing device.

2. The method of claim 1, wherein the software program comprises embedded software.

3. The method of claim 1, further comprising:
establishing the peer-to-peer connection with the second computing device using Wi-Fi Direct protocol.

4. The method of claim 1, further comprising:
upon determination that the second version of the software program is more recent than the first version of the software program, storing a version number associated with the second version of the software program.

5. The method of claim 1, further comprising, upon determination that the first version of the software program is more recent than the second version of the software program, transmitting first installation software associated with the first version of the software program to the second computing device.

6. The method of claim 1, further comprising, upon determination that the first version of the software program is the same as the second version of the software program:
terminating the peer-to-peer connection with the second computing device;
establishing a second peer-to-peer connection with a third computing device from among the one or more computing devices;
comparing the first version of the software program installed on the first computing device to a third version of the software program installed on the third computing device; and
upon determination that the third version of the software program is more recent than the first version of the software program, receiving third installation software associated with the third version of the software program and executing the third installation software to install the third version of the software program onto the first computing device.

7. The method of claim 1, further comprising:
periodically performing the steps of the method at a predetermined interval.

8. A device comprising:
one or more processors; and
one or more non-transitory memory modules communicatively coupled to the one or more processors and storing machine-readable instructions that, when executed, cause the one or more processors to at least:
detect a plurality of computing devices remote from the device, each of the plurality of computing devices is associated with a different hospital bed;
automatically establish a peer-to-peer connection with each of the plurality of computing devices;
compare a version of a software program installed on the device associated with a first hospital bed and versions of the software program installed on each of the plurality of computing devices;
determine which of the device and the plurality of computing devices has the most recent version of the software program; and
upon determination that one of the plurality of computing devices has the most recent version of the software program, receive installation software associated with the most recent version of the software program from the one of the plurality of computing devices determined to have the most recent version of the software program, and execute the installation software to install the most recent version of the software program onto the device.

9. The device of claim 8, wherein the instructions further cause the one or more processors to:
store the installation software; and
transmit the installation software to each of the plurality of computing devices that does not have the most recent version of the software program.

10. The device of claim 8, wherein the instructions further cause the one or more processors to:
store a version number associated with the most recent version of the software program.

11. The device of claim 8, wherein the instructions further cause the one or more processors to:
upon determination that the device has the most recent version of the software program, transmit the installation software associated with the most recent version of the software program to each of the plurality of computing devices that does not have the most recent version of the software program.

12. The device of claim 8, wherein the software program comprises embedded software.

13. The device of claim 8, wherein the instructions further cause the one or more processors to:
establish the peer-to-peer connection with each of the plurality of computing devices using Wi-Fi Direct protocol.

14. A system comprising a first computing device and a second computing device remote from the first computing device, wherein:
the first computing device associated with a first hospital bed is configured to:
detect the second computing device associated with a second hospital bed;
automatically establish a peer-to-peer connection with the second computing device;
compare a first version of a software program installed on the first computing device to a second version of the software program installed on the second computing device; and
upon determination that the second version of the software program is more recent than the first version of the software program, transmit a request to the second computing device for second installation software associated with the second version of the software program, receive the second installation software from the second computing device in response to the request, and execute the second installation software to install the second version of the software program onto the first computing device; and
wherein the second computing device is configured to:
establish the peer-to-peer connection with the first computing device;
receive the request for the second installation software from the first computing device; and transmit the second installation software to the first computing device in response to the request.

15. The system of claim 14, wherein the first computing device is further configured to:
   establish the peer-to-peer connection with the second computing device using Wi-Fi Direct protocol.

16. The system of claim 14, wherein the first computing device is further configured to:
   upon determination that the second version of the software program is more recent than the first version of the software program, store a version number associated with the second version of the software program.

17. The system of claim 14, wherein the first computing device is further configured to:
   upon determination that the first version of the software program is more recent than the second version of the software program, transmit first installation software associated with the first version of the software program to the second computing device.

18. The system of claim 14, wherein the first computing device is further configured to, upon determination that the first version of the software program is the same as the second version of the software program:
   terminate the peer-to-peer connection with the second computing device;
   establish a second peer-to-peer connection with a third computing device;
   compare the first version of the software program installed on the first computing device to a third version of the software program installed on the third computing device; and
   upon determination that the third version of the software program is more recent than the first version of the software program, receive third installation software associated with the third version of the software program and execute the third installation software to install the third version of the software program onto the first computing device.

\* \* \* \* \*